United States Patent [19]  [11]  4,356,164
Tabor et al.  [45]  Oct. 26, 1982

[54] DETECTION OF NON-A, NON-B HEPATITIS ASSOCIATED ANTIGEN

[75] Inventors: Edward Tabor, Rockville; Robert J. Gerety, Potomac, both of Md.

[73] Assignee: Govt. of the U.S., as represented by the Secretary, Dept. of Health & Human Services, Washington, D.C.

[21] Appl. No.: 40,921

[22] Filed: May 21, 1979

[51] Int. Cl.³ .................... G01N 33/56; G01N 33/58
[52] U.S. Cl. ..................................... 424/1; 23/230 B; 424/12
[58] Field of Search ..................... 424/1, 12; 23/230 B

[56] References Cited

U.S. PATENT DOCUMENTS 3,867,517  2/1975  Ling ............................ 424/1

OTHER PUBLICATIONS

Shirachi et al., The Lancet, Oct. 21, 1978, pp. 853–856.
Gocke et al., S. Immunology, vol. 104, Apr. 1970, pp. 1031–1032.
Tabor et al., Gastroenterology, 76:680–684, 1979.
Tabor et al., The Lancet, Mar. 4, 1978, pp. 463–466.
Tabor et al., From Viral Hepatitis, Ed. Vyas et al., Franklin Institute Press, Philadelphia, 1978, pp. 419–421.

Primary Examiner—Christine M. Nucker
Attorney, Agent, or Firm—John S. Roberts, Jr.

[57] ABSTRACT

In the detection of the highly transmittable agent of non-A, non-B hepatitis there is described a method utilizing antigen-antibody reaction and a preferred counterelectrophoresis method for the detection of said antigen. The method may be applied as in the recipients of blood transfusions and also may be applied to screening blood donors where the blood donor had transmitted by transfusion non-A, non-B hepatitis antigen several years previously or there was at least a 1–5 year retrospective period from donating blood to retention of active transmittable agent.

9 Claims, No Drawings

DETECTION OF NON-A, NON-B HEPATITIS ASSOCIATED ANTIGEN

INTRODUCTION

The present invention is concerned with the discovery of the existence of a non-A, non-B hepatitis associated antigen and this invention is also concerned with the use of this antigen to identify infectious blood donors and to prepare a vaccine. It is realized that in the time span after the discovery of the existence by the present inventors, there appeared an article by Shirachi et al, "Hepatitis 'C' Antigen in Non-A, Non-B Post-Transfusion Hepatitis," The Lancet, Oct. 21, 1978, pages 853–856.

In recent studies non-A, non-B hepatitis has been found to occur in 10% of transfused patients in the United States, resulting in about 200,000 cases per year. Fatalities from non-A, non-B hepatitis in the United States probably number around 1,000 per year among transfusion-related cases.

PRIOR ART STATEMENT

Shirachi et al, The Lancet, Oct. 21, 1978, pages 853–856.

Tabor et al, Viral Hepatitis, eds. G. N. Vyas et al, The Franklin Institute Press, Philadelphia, 1978, pages 419–421.

Tabor et al, The Lancet, Mar. 4, 1978, pages 463–466.

Tabor et al, Gastroenterology, 76:680–684, 1979.

Gocke et al, The Journal of Immunology, 104(4): 1031–1032, April 1970.

THE NON-A, NON-B ANTIGEN AND ITS ANTIBODY

Many cases of acute and chronic hepatitis which do not result from infection by either hepatitis A virus (HAV) or hepatitis B virus (HBV), are called "non-A, non-B hepatitis," and now account for 89% of cases of post-transfusion hepatitis in the United States. The presence of a transmissible agent in this disease has been demonstrated by its transmission to chimpanzees by the inoculation of serum from humans chronically infected with non-A, non-B hepatitis, and by serial passage to additional chimpanzees. Recently an antigen-antibody system detected by counter-electrophoresis (CEP) was described in humans with post-transfusion non-A, non-B hepatitis (Shirachi, et al, supra). In the present invention is reported antigen which is detectable by CEP in the serum of chimpanzees during the acute phase of experimentally induced human non-A, non-B hepatitis, an antibody which appears during convalescence, and the detection of this antigen-antibody system in humans with non-A, non-B hepatitis.

The activity of the antigen has been shown in counterelectrophoresis (CEP) as well as in a solid phase radioimmunoassay.

Additionally, human tests showed antigen activity up to 1–5 years after transfusion in the donor. The tests enable blood banks to idenfity blood donors whose blood may transmit non-A, non-B hepatitis to recipients and eliminate the use of their blood for transfusion. This results in a decrease in the incidence of this disease. The test is also used to diagnose non-A, non-B hepatitis in patients.

An antigen was detected by counterelectrophoresis in serum samples from six of seven chimpanzees during the acute phase of experimentally induced non-A, non-B hepatitis using antiserum from a chimpanzee convalescent from human non-A, non-B hepatitis. This antigen could not be detected prior to the transfusion in 35 pre-inoculation serum samples from these chimpanzees, or in 94 weekly bleedings from three chimpanzees with hepatitis A and three chimpanzees with hepatitis B.

The antigen was also detected in each of two serum samples obtained from a human with chronic hepatitis whose blood had transmitted non-A, non-B hepatitis to a nurse by accidental needlestick and to chimpanzees by experimental inoculation. In addition, the antigen was detected in serum obtained retrospectively from 11 of 31 former blood donors whose blood had transmitted post-transfusion non-A, non-B hepatitis several years previously to recipients of a single unit of their blood.

Antibody to this antigen was detected in convalescent serum samples from all seven chimpanzees studied, in convalescent serum from the nurse infected by accidental needlestick, and in serum from a hemodialysis patient convalescent from non-A, non-B hepatitis.

COUNTERELECTROPHORESIS

Counterelectrophoresis (CEP) which may be also described as immunoelectrosmophoresis (IEOP) or immunoelectrodiffusion (IED) or countercurrentelectrophoresis is utilized as follows.

Sera stored at $-20°$ C. were tested by CEP using 1% agarose (Indubiose A37, L'industrie Biologique Francaise, Gennevilliers, France) in barbital buffer, pH 8.6, poured onto $3.5 \times 12.5$ cm glass plates (16 ml per plate). Melted agarose (16 ml) was poured onto a lantern slide. When it had cooled, two rows of holes were punched in the agarose. Antibody was placed in one row of holes and samples to be tested were added to the other row. When testing for antibody, antigen was added to one row and samples in the other row. The lantern slide was placed in a CEP chamber. Paper wicks were used to connect each side of the slide to each of two pools of barbital buffer, pH 8.6. An electric current was passed across the plate, 35 milliamps per plate, for one hour. Immunoprecipitin lines were read after 1, 24, and 48 hours of storage in a moist chamber at room temperature. When the test sample was positive, a precipitin line was seen between the rows, using the naked eye with the aid of an electric lamp.

RADIOIMMUNOASSAY (RIA)

Antibody to the non-A, non-B hepatitis was purified by precipitating it from serum using 30% ammonium sulfate. This purified antibody was labeled with radioactive iodine using the chloramine-T method. Unpurified antibody was coated on plastic beads. The coated beads were placed in wells of a plastic plate. Samples to be tested for antigen were added to each well. After 18 hours incubation, the excess sample (other than any antigen which was then attached to the bead) was washed away. The radio-labeled purified antibody was then added to the wells and incubated for three hours; the excess was washed away. The amount of radioactivity adhering to the beads was counted in gamma counter. Positive results were identified by the detection of radioactivity on the beads, in comparison to negative samples. The presence of antibody was determined by adding the sample to be tested to a known antigen-positive serum, and then, following incubation for one hour, testing the mixture for antigen. The presence of antibody was identified by the decrease in radioactive counts compared to the result obtained using the antigen alone.

In addition to CEP and RIA used to detect antigen and antibody, alternate immunological methods may be used to detect the antigen including agar gel diffusion, passive hemagglutination, latex agglutination, complement fixation, and enzyme linked immuno-sorbent assay.

THE ANTIGEN

An abbreviated or capsulized description of purification for the associated antigen and active subunits is summarized as follows.

The non-A, non-B hepatitis associated antigen was purified from serum (or tissue and cell cultures when the agent is propogated) by selection from the following techniques:

(1) Fractional (selective) precipitation or solubilization
(2) Gel filtration, molecular sieving
(3) Chromatographic techniques (affinity, adsorption or ion-exchange chromatography)
(4) Density gradient centrifugation
(5) Electrophoresis including isotachophoresis and isoelectric focusing
(6) Countercurrent distribution Further purification treatments include alterations in pH, chemical treatments and enzyme treatments.

Subunits

Immunologically active subunits of the non-A, non-B hepatitis associated antigen have been prepared following preliminary purification of the antigen by a selection from the following:
(1) detergent treatment
(2) limited hydrolysis
(3) reduction Immunologically active polypeptides have been separated here by procedures outlined above.

Development of In Vitro Tests

By inducing antibody specific for the non-A, non-B associated antigen in suitable animal species; i.e., chimpanzees, or selecting human sera containing these antibodies, immunologic tests to detect the antigen (such as Agar gel diffusion, counterelectrophoresis, complement fixation, passive hemagglutination, radioimmunoassay or enzyme-linked immuno-sorbent assay) have been developed and used to (1) detect persons transmitting non-A, non-B hepatitis and (2) identify sources of antigen for in vitro tests and vaccine production.

Vaccine

A direct use of purified antigen or immunologically active subunits inactivated by either heat, formalin or both may be conventionally utilized as a vaccine.

The table below shows a summary of clinical testing.

TABLE 1

| | Patients Tested | Non-A, Non-B Antigen | Antibody |
|---|---|---|---|
| 54 | Normal volunteer blood donors | 0 | Not tested |
| 3 | Humans with chronic non-A, non-B hepatitis who transmitted the disease to humans and chimpanzees | 3 | 0 |
| 31 | Blood donors who transmitted non-A, non-B hepatitis one to four years previously | 11 | 5 |
| 12 | Humans with non-A, non-B hepatitis (weekly samples) | 8 | Not tested |
| 2 | Humans who recovered from non-A, non-B hepatitis | 0 | 2 |
| 152 | Hemophiliac patients | Not tested | 59 |

EXAMPLE 1

Serum samples were obtained from three humans with chronic non-A, non-B hepatitis. Blood from human #1 had caused non-A, non-B hepatitis in a nurse who accidentally cut herself on a piece of glass contaminated with his blood. Humans #2 and #3 had donated blood, and their blood had caused non-A, non-B hepatitis in recipients. Serum from all three (humans #1, #2, and #3) was inoculated into chimpanzees and caused non-A, non-B hepatitis in the chimpanzees. The non-A, non-B hepatitis associated antigen was found in the blood of all three humans.

EXAMPLE 2

Serum samples were obtained from 31 blood donors whose blood had caused non-A, non-B hepatitis in patients who had been transfused with a single unit of their blood (and no other blood) one to four years previously. The non-A, non-B hepatitis associated antigen was detected in 11 of these donors.

EXAMPLE 3

Serum was tested from 54 normal blood donors. None had the non-A, non-B hepatitis associated antigen.

EXAMPLE 4

Five of the 31 implicated blood donors (confer Example 2) had antibody to the non-A, non-B associated antigen, but no detectable antigen. The antibody in these cases indicated the presence of a different stage of disease and was also an indication that in some cases their blood would transmit the disease, as it had done previously.

EXAMPLE 5

Chimpanzee Studies

Weekly serum samples from seven chimpanzees beginning four weeks before inoculation with human non-A, non-B hepatitis were tested. The inoculation and course of infection in these chimpanzees are described in the three Tabor et al articles noted in the Prior Art Statement, supra. Each chimpanzee was infected by intravenous inoculation of serum from one of three humans chronically infected with non-A, non-B hepatitis. Chimpanzees #922, #930, #911, #916, and #946 were infected by inoculation with Inoculum I, or with acute phase serum from a chimpanzee infected by Inoculum I (Inoculum I passage). Chimpanzee #918 was infected by Inoculum II and #919 by Inoculum III. A convalescent serum from each chimpanzee was used as antibody in CEP against that chimpanzee's own weekly serum samples; in three chimpanzees (#922, #918, #919), the convalescent serum was obtained after two intravenous inoculations with infectious serum. In addition, convalescent serum from chimpanzee #922 was used to test all chimpanzee serum samples studied.

Results. The antigen was detected in the sera of six of seven chimpanzees during non-A, non-B hepatitis. In general, the antigen was detected during the time of elevated aminotransferase levels but without a strict correlation with histopathologic changes in liver biopsy specimens. Chimpanzee #922 (Inoculum I) had elevated aminotransferase levels from Week 2 to 16 and had antigen detectable at Weeks 4-9 and at Week 15. Chimpanzee #930 (Inoculum I) had elevated aminotransferase levels from Week 3 to 23 and had antigen detectable at Weeks 2-8 (including two serum samples shown to transmit non-A, non-B hepatitis to experimentally inoculated chimpanzees) and at Week 18. Chimpanzee #911 (Inoculum I passage) had elevated aminotransferase levels from Week 5 to 21 and had antigen detectable at Weeks 19 and 20. Chimpanzee #946 (Inoculum I passage) had elevated aminotransferase levels from Week 3 to 11 and had antigen detectable at Weeks 9, 10, 12, and 16. Chimpanzee #918 (Inoculum II) had elevated aminotransferase levels from Week 4 to 20 and had antigen detectable at Weeks 6, 11, 14, and 15. Chimpanzee #919 (Inoculum III) had elevated aminotransferase levels from Week 3 to 20 and had antigen detectable at Week 3. The antigen could not be detected in serum samples from Chimpanzee #916 (Inoculum I passage).

The antigen could not be detected in any of 35 preinoculation serum samples from these chimpanzees, nor could it be detected in 28 weekly bleedings from three chimpanzees during experimentally induced hepatitis A or in 66 weekly bleedings from three chimpanzees during experimentally induced hepatitis B.

Antibody was detected in convalescent serum samples from all seven chimpanzees. Antibody was detected in every serum sample from chimpanzee #922 beginning with Week 28 after inoculation, 13 weeks after the disappearance of antigen and the return of aminotransferase levels to near normal values. Antibody remained detectable until longer than 19 months after inoculation. Titrations performed on selected serum samples from chimpanzee #922 before and after a second intravenous exposure to a non-A, non-B hepatitis inoculum (Inoculum III), revealed a four-fold increase in antibody titer. Ammonium sulfate precipitation and DEAE cellulose chromatography revealed the antibody to be in the 7S (IgG) fraction.

EXAMPLE 6

Human serum used as antibody in CEP included convalescent serum from the nurse (Human #1) who had recovered from non-A, non-B hepatitis 4 years earlier after the needlestick exposure to Inoculum I and convalescent serum from a multiply-transfused hemodialysis patient with a history of non-A, non-B hepatitis (Human #2).

Results. The antibody was detected in convalescent serum from Human #1 and Human #2. Antibody was not detected in any of two serum samples from the patient with chronic non-A, non-B hepatitis whose serum became Inoculum I.

We claim:

1. A method of assaying for the amount of non-A, non-B hepatitis antigen present in a sample comprising a first step of reacting antigen in the sample with the antibody, a second step of separating reactive phase from non-reactive phase by precipitating antibody from serum and purifying said antibody, and a third step of measuring the extent of the reaction as a measurement of the amount of non-A, non-B hepatitis antigen present in the sample.

2. The method of assaying according to claim 1 wherein the separation of antigen is made by means of counterelectrophoresis.

3. The method of assaying according to claim 1 wherein the purified antibody is labeled radioactively with a radioactive tracer and the measurement of antigen is made by detecting the radioactivity in the precipitated antibody.

4. The method of assaying according to claim 3 wherein the radioactive tracer is radioactive iodine.

5. The method of assaying according to claim 1 wherein the separation of antigen is made by means of agar gel diffusion, which method depends on relative motion of the molecules through the gel where antigen is placed above a column of antibody.

6. The method of assaying according to claim 1 wherein the separation of antigen is made by means of passive hemagglutination where the presence of a particular antigen is signaled by precipitation or agglutination of erythrocytes which have antigen attached.

7. The method of assaying according to claim 1 wherein the presence of a particular antibody causes a reaction of antigen in latex.

8. The method of assaying according to claim 1 wherein the separation of antigen is made where the complement, a lytic substance in serum, is fixed when reacted with an antigen/antibody complex.

9. In a retrospective period of hepatitis infection preceding transfusion to the donor in the range of 1-5 years, a method of detecting in the serum of a donor the presence of an antigen in non-A, non-B hepatitis by means of an antigen-antibody reaction of claim 1.

* * * * *